United States Patent [19]
Withers et al.

[11] Patent Number: 5,259,501
[45] Date of Patent: Nov. 9, 1993

[54] PERSONAL USE SYRINGE COLLECTING AND DISPOSING SYSTEM

[75] Inventors: L. Andrew Withers, Atlanta; David W. Hughes, Chamblee, both of Ga.

[73] Assignee: McDonald, Withers & Hughes, Inc., Atlanta, Ga.

[21] Appl. No.: 757,132

[22] Filed: Sep. 10, 1991

[51] Int. Cl.$^5$ .............................................. B65D 83/00
[52] U.S. Cl. ..................... 206/366; 206/370; 220/229; 220/620; 220/689
[58] Field of Search ............... 206/364, 365, 366, 370; 220/229, 620, 689, 908

[56] References Cited

U.S. PATENT DOCUMENTS

| | | | |
|---|---|---|---|
| 746,815 | 12/1903 | Ghirardelli | 220/620 |
| 1,607,923 | 11/1926 | Sebell | 220/620 |
| 1,643,252 | 9/1927 | McCrery | 220/620 |
| 3,072,517 | 1/1963 | Gaylord | 220/620 |
| 3,086,674 | 4/1963 | Scheuerman | 220/229 |
| 3,292,776 | 12/1966 | Penn | 206/43 |
| 3,543,996 | 12/1970 | West | 220/620 |
| 3,637,072 | 1/1972 | Narusawa et al. | 206/365 |
| 4,328,904 | 5/1982 | Iverson | 220/229 |
| 4,351,434 | 9/1982 | Elisha | 206/366 |
| 4,375,849 | 3/1983 | Hanifi | 206/366 |
| 4,454,944 | 6/1984 | Shillington et al. | 220/229 |
| 4,485,918 | 12/1984 | Mayer | 206/366 |
| 4,520,926 | 6/1985 | Nelson | 206/370 |
| 4,657,138 | 4/1987 | Watson | 206/366 |
| 4,736,844 | 4/1988 | Scott et al. | 206/370 |
| 4,767,008 | 8/1988 | Warnecke et al. | 206/570 |
| 4,848,587 | 7/1989 | Nipp | 206/571 |
| 4,969,554 | 11/1990 | Sawaya | 206/370 |
| 5,020,665 | 6/1991 | Bruno | 206/365 |
| 5,024,326 | 6/1981 | Sandel et al. | 206/364 |
| 5,039,004 | 8/1991 | Simpson | 206/366 |
| 5,065,939 | 11/1991 | Boothe et al. | 206/366 |
| 5,152,394 | 10/1992 | Hughes | 206/366 |
| 5,163,375 | 11/1992 | Withers et al. | 206/366 |
| 5,167,193 | 12/1992 | Withers et al. | 206/360 |

FOREIGN PATENT DOCUMENTS 2040268  8/1980  United Kingdom .

OTHER PUBLICATIONS

The Microban Effect in Health Care Products Inherent Protection Against Hospital Cross-Contamination (Leaflet) by Microban Products Co. 1983.

Primary Examiner—David T. Fidei
Attorney, Agent, or Firm—Hopkins & Thomas

[57] ABSTRACT

The system (10) for collecting and disposing of personal-use hypodermic syringes (29) comprises a cylindrical container (11) and a telescopic cover 12. The container (11) includes a side wall (15) defining a collection chamber (19) for collecting used hypodermic syringes (29). The telescopic cover (12) includes an inner top wall (25) and an outer top wall (26) having an opening (28) therein, which is of sufficient internal breadth sized and shaped specifically for receiving hypodermic syringes (29). The used syringes (29) will be pushed through a scored portion (30) of the inner top wall (25), and then a barrel (31) portion of the syringe fits through the opening (28) formed by the outer top wall (26). The container (11) is sized and shaped so that once deposited in the collection chamber (19), the syringes (29) cannot turn end-for-end.

27 Claims, 3 Drawing Sheets

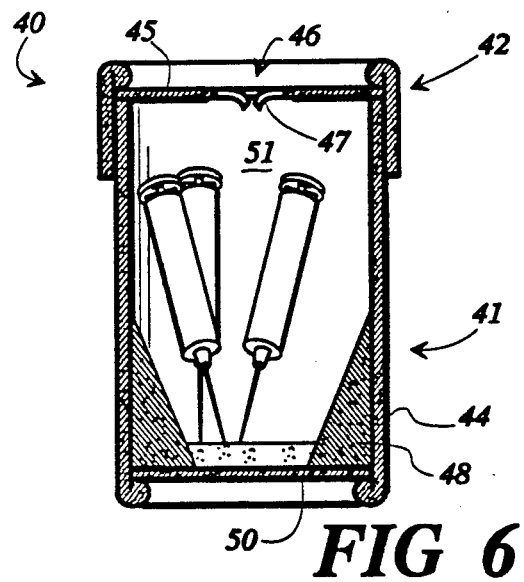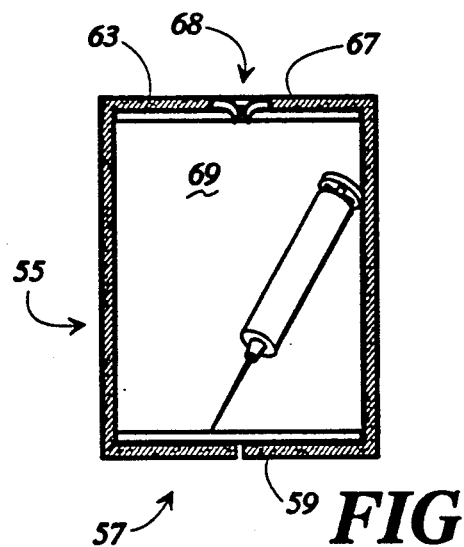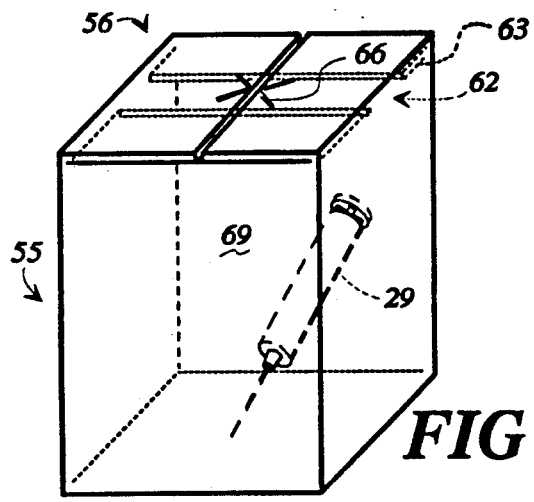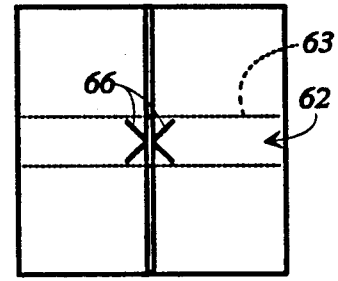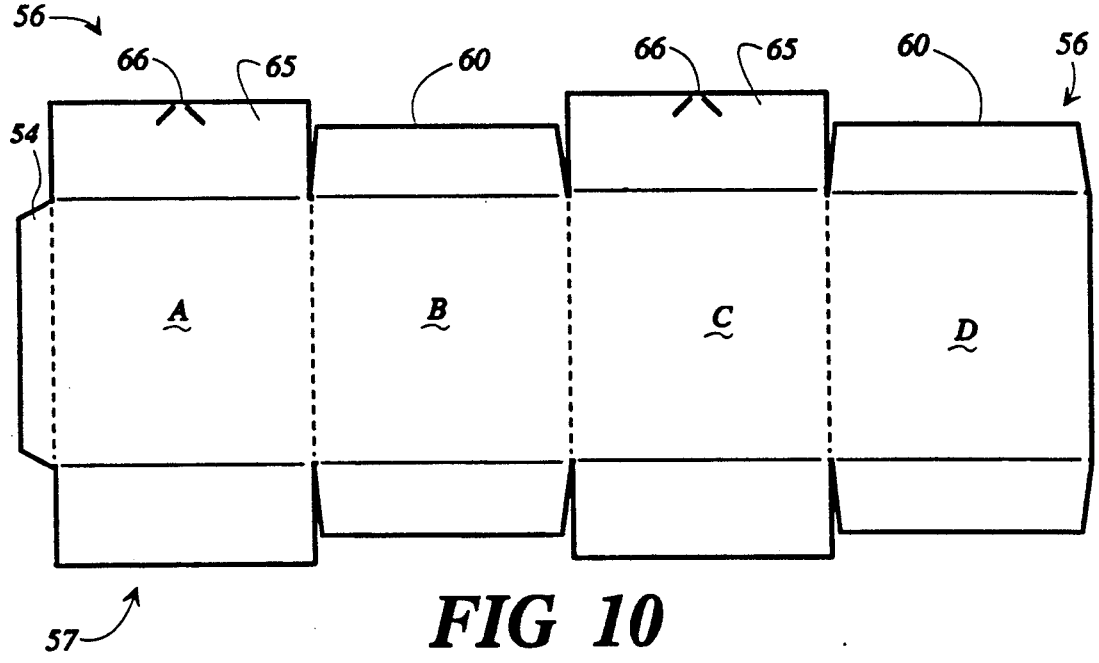

PERSONAL USE SYRINGE COLLECTING AND DISPOSING SYSTEM

FIELD OF THE INVENTION

The present invention relates in general to a system for collecting and disposing of medical wastes. More particularly, the invention relates to a home-use system for collecting and disposing of hypodermic needle syringes, such as insulin needle syringes used by diabetic persons.

BACKGROUND OF THE INVENTION

Hypodermic needle syringes often are used in home and away from home environments and other non-medical institution environments by persons such as diabetic patients who must control their medical condition by insulin therapy, whereby a person receives injections one or more times a day. Typically, insulin and other medical injections are self-administered and hypodermic needle syringes generally must be supplied to the receiver for use in the home, work place, or travel environment.

Disposable or one-use needle syringes of the type used for injecting insulin into diabetics are available by subscription from a physician and typically are formed of a uniform shape and size. The standard disposable syringe employs a plunger which is drawn back from one end of the syringe barrel to fill the syringe through the needle which is held within a vial of insulin during a filling operation of the syringe. After injection, the used insulin needle syringes should be safely collected and disposed of without presenting a hazard to other members of the family or community.

Presently, the prior art discloses many different collectors for collecting medical sharps and other medical wastes, however, none of the known prior art discloses a collector or receptor designed specifically for use at home and while away from home for collecting and disposing of hypodermic syringes, such as insulin needle syringes. Thus, diabetics typically discard used insulin needle syringes into a generic collector, such as a cardboard box or an empty plastic milk jug or directly into a generic household garbage can, all of which usually are delivered to a local refuse collection facility. During containment and transfer of the garbage and hypodermic syringes to a waste collection facility, there is a hazard that the hypodermic syringes might contaminate family members or workers who are handling the garbage. Experience demonstrates that the skin scratch or puncture by the needle of the syringes have caused occasional injury to people who are in the environment of a diabetic patient.

For example, when the garbage bag is filled with household trash, including hypodermic syringes and is being transported, the needle of the syringe can protrude through its generic cardboard box or milk jug and the garbage bag to scratch or puncture a family member who is transporting the garbage from a room in the house to the household garbage disposal area, or to scratch or puncture a worker who is collecting the trash to a local waste collection facility.

Therefore, it would be advantageous to provide a disposable, puncture-resistant container designed specifically for safely collecting and disposing of hypodermic syringes in a personal environment, such as home, work place, or travel environment.

SUMMARY OF THE INVENTION

Briefly described, the present invention comprises a system for collecting and disposing of hypodermic syringes in a non-medical institution or personal environment. A preferred embodiment of the invention comprises a puncture-resistant, leak-resistant, cylindrically-shaped container. One end of the container includes an opening which corresponds in breadth and shape to the cross-sectional breadth and shape of the insulin syringe, so as to receive insulin syringes when inserted longitudinally through the opening. Moreover, the container is sized, shaped, and designed for receiving a predetermined number of syringes, and the breadth of the container is less than the length of the syringes so that once deposited into the container the syringes cannot turn end-for-end inside the container. Additionally, the container can be fabricated of a biodegradable and combustible material of sufficient volume so that when the container is filled with its capacity of used syringes and is incinerated, the material of the container will ignite and render the syringes to a non-combustible ash.

Another embodiment of the container includes a rectangularly-shaped collection chamber with an end wall means that is formed of overlying flaps. A first set of opposing flaps of the top wall form a space that corresponds to the largest cross-sectional breadth of a syringe, and another two opposing set of flaps overlaps the first set of flaps and is also sized and shaped to correspond to the largest cross-sectional breadth of the syringe. The embodiment is formed so that two opposing flaps can act as an opening for preventing insertion of objects larger than a home-use hypodermic syringe into the collection chamber of the container.

In another embodiment of the invention, four side walls of the container form a rectangularly-shaped container with a rectangularly-shaped collection chamber. An opening in an end wall for receiving used syringes is of approximately the same cross-sectional size and shape of the used hypodermic syringe so that in order to deposit the syringe through the opening, the syringe must be oriented and positioned in accordance with the orientation and position of the opening. Additionally, this embodiment provides a double-end wall construction so that both the needle point of the syringe and the end opposite the needle point face a dual-wall construction so that both the needle point of the syringe and the end opposite the needle point face a dual-wall when the needles have been inserted in the container. The size and shape of the container will be tailored so that once the used hypodermic syringes are deposited into the collection chamber, the used syringes will not turn end-for-end. Thus, the container maintains the used syringes in the same general orientation as when deposited into the collection chamber and provides a dual-end wall so that the hypodermic syringes will be safely container within the container.

In another embodiment of the present invention, four side walls and opposed end walls of the container form a rectangular collection chamber, and an elongated opening in a side wall is sized and shaped specifically for a hypodermic syringe to be diagonally inserted in the opening. The diagonal insertion causes the hypodermic syringes to be contained in the container with the needle points of the syringes positioned in substantially the same direction and with the deposited syringes to lying in a horizontal position. Moreover, the container will be sized and shaped so that once deposited into the collection chamber, the used syringes will not turn end-for-end, thus maintaining the syringes in the same general orientation as when inserted int the collection chamber.

A needle receptacle can be inserted in any of the embodiments of the invention adjacent and end wall for receiving the needles of the syringes. Typically, the needle receptacle includes a surface which tends to direct the needles toward the central longitudinal axis of the container, causing the barrels and plungers of the used syringes deposited in the collection chamber to slope outwardly from the center of the collection chamber. Additionally, the insert can be textured to be penetrated by the needle points o the syringes. The insert also can be formed of a combustible material so that if the container is incinerated, the insert will burn and will enhance combustion of the container and the used syringes within the collection chamber.

All of the embodiments can include indicia which identify the container as a hazardous items disposal area. The indicia is located on the exterior side of the container, and can designate personal-use hypodermic syringes by methods, such as color-coding, labelling, a counter-mechanizm, and serializing the container, or texturing the container for visually-impaired people, or any combination of the methods thereof. Thus, the people who are in the environment of a personal hypodermic syringe user are less likely to tamper with the container and the used syringes inside the container.

All of the above-mentioned embodiments can be specifically designed for a predetermined number of syringes and can include an accounting system for determining the number of used syringes deposited in the collection chamber of the container. Such means of accounting for the used syringes can include a transparent end wall means for visual inspection and counting of the number of used syringes in the container, weighing the container filed with used syringes so as to confirm a predetermined mass of the used syringes, and radiation inspection, such as by x-raying the container to inspect the number of used syringes deposited in the collection chamber of the container.

The container can be supported by a wall bracket support so that the container can be mounted in a predetermined position, but also can be removed from the wall bracket and carried by a person in a purse, suit case, or the like, replaced or transportable to other convenient places such as in a car, work place, and the like. Additionally, the container can be attached semi-permanently to a surface in these environments by such means as adhesives.

It is therefore an object of the present invention to provide an apparatus which safely and conveniently collects, contains, and disposes of hypodermic needle syringes in a personal environment, such as the home, work place and travel environments.

Another object of the present invention is to provide an improved container which is suitably sized, shaped and placed to safely and expediently receive a predetermined number of home-use syringes, such as of insulin needle syringes used by diabetic persons.

A further object of the present invention is to provide such a system for safely collecting and disposing of hypodermic needle syringes, whereby the container is formed of a puncture-resistant and leak-resistant material.

Another object of the present invention is to provide a container for personal use for receiving and disposing of needle hypodermic syringes, which can be fabricated of materials compatible with the use and expedient manufacture of the container.

It is yet another object of the present invention to provide a container which can be fabricated of a combustible and biodegradable material so that if incinerated, the container will not evolve toxic substances to the environment.

A further object of the present invention is to provide a container which has an opening sized and shaped specifically for receiving home-use hypodermic needle syringes.

It is yet another object of the present invention to provide a container which has an opening sized and shaped specifically for receiving home-use hypodermic needle syringes.

It is yet another object of the present invention to provide a container designed to hold a predetermined number of hypodermic needle syringes in substantially the same orientation as when inserted into the collection chamber of the container so that the used syringes cannot turn end-for-end.

A further object of the present invention is to provide a container designed to hold a predetermined number of hypodermic needle syringes with the needle points of the syringes oriented in substantially the same direction.

Another object of the present invention is to provide means for accounting for the used syringes as they are being deposited and fill up the collection chamber of the container.

A more complete understanding of the present invention will be had by those skilled in the art, as well as an appreciation of additional advantages which will become apparent upon reading the detailed description of the preferred embodiment and examining the drawings, the following of which is a brief description.

BRIEF DESCRIPTION OF THE DRAWINGS

FIG. 6 is a side cross-sectional view of another embodiment of the present invention showing a single-top wall means and an insert.

FIG. 7 is a side cross-sectional view of another embodiment of the invention with a used syringe deposited in the collection chamber of the container.

FIG. 8 is a perspective view of the embodiment of FIG. 7.

FIG. 9 is a plan view of the embodiment of FIG. 7.

FIG. 10 is a plan view of the embodiment of FIG. 7 shown unassembled.

DETAILED DESCRIPTION OF THE INVENTION

Figure 1:
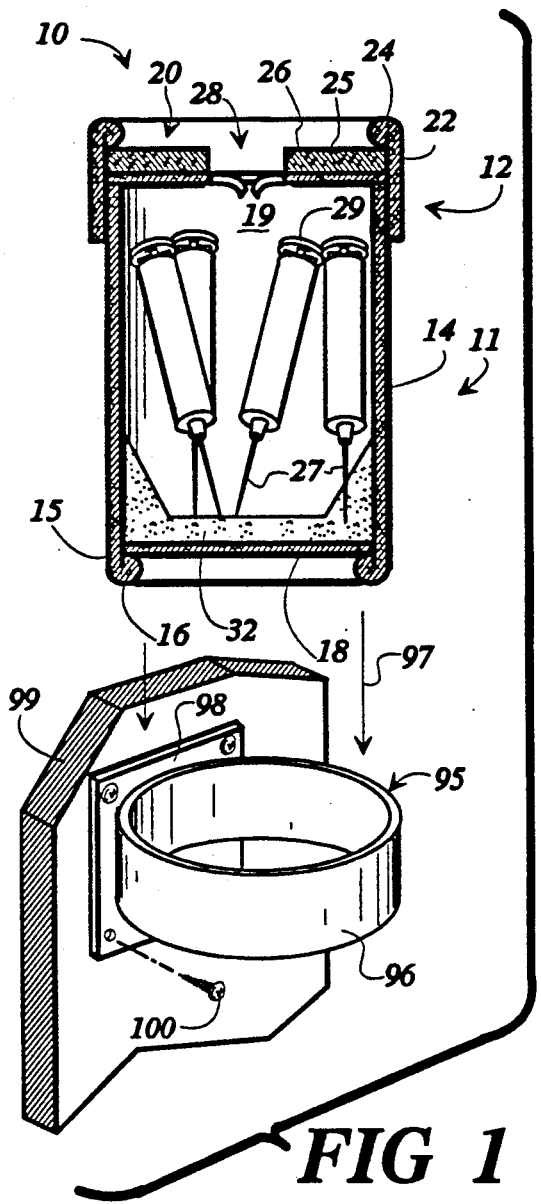
FIG. 1 is a side cross-sectional view of the hypodermic needle syringe container and its insert.

Referring now in more detail to the drawings in which like numerals indicate like parts throughout the several views, FIG. 1 illustrates the hypodermic needle syringe collecting and disposing system 10, which includes a cylindrical container 11. The container 11 is shown separated from its wall mount 95 and ready for insertion into a circular sleeve 96 of the wall mount 95 as indicated by downward directional arrows 97. The wall mount 95 comprises a mounting bracket 98, preferably attached to a wall 99 by adhesives (not shown) or by multiple screws 100 which extend through openings of the bracket into the wall of the building. The mounting bracket 98 supports the circular sleeve 96 in an upright attitude. The container 11 comprises an upper telescoping cover 12 which telescopes about a lower cylindrical body 14. The lower cylindrical body 14 includes a lower cylindrical side wall 15 with the lower end portion of the side wall 15 turned inwardly to form a circular flange or seat 16 and a bottom wall 18 is positioned inside the side wall 15 and is supported by the seat 16. The bottom wall 18 can be formed of a puncture-resistant and leak-resistant material. The cylindrical side wall 15 and bottom wall 18 define a collection chamber 19 in which is bound by a top wall means 20 of the telescoping cover 12.

Figure 3:
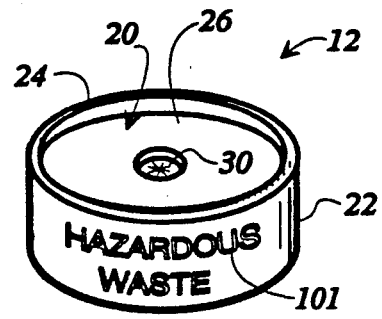
FIG. 3 is a perspective view of a dual-top wall means of the embodiment of FIG. 1.
Figure 4:
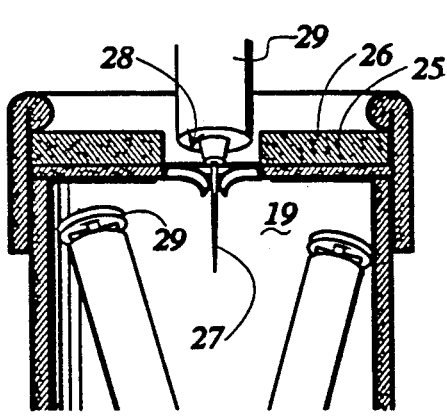
FIG. 4 is a side cross-sectional view of a needle of a hypodermic syringe being inserted through the dual-top wall means of the container of FIG. 1.
Figure 5:
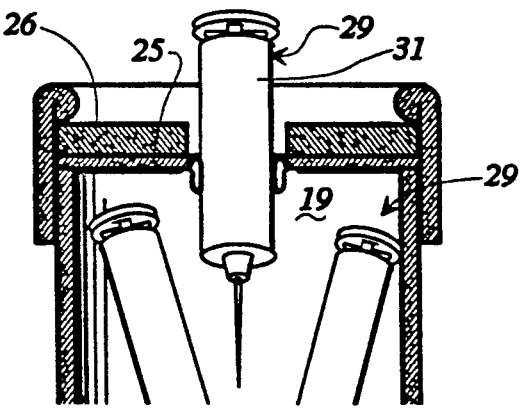
FIG. 5 is a side cross-sectional view of a syringe barrel being inserted through the dual-top wall means of the container of FIG. 1.

The telescoping cover 12 has a cylindrical side wall 22 which is of sufficient internal breadth to tightly fit over an upper end of the cylindrical side wall 15 as shown in FIGS. 1 and 3. The telescoping cover 12 includes an inwardly projecting circular seat 24 supporting the top wall means 20. In this embodiment, the top wall means 20 comprises an inner top wall 25 and an outer top wall 26. The outer top wall defines an opening 28 that is of sufficient internal breadth and sized and shaped for receiving a home-use hypodermic syringe 29 (FIGS. 4 and 5). As shown in FIGS. 4 and 5, a needle point 27 of the longitudinally oriented syringe 29 when deposited into the collection chamber 19, first punctures a scored portion 30 (FIG. 3) of the inner top wall 25 (FIG. 4), and then a barrel 31 portion of the syringe fits through the opening 28 formed by the outer top wall 26, when the hypodermic syringe is pushed through the opening and into the collection chamber 19. The dual top-wall construction allows users of personal hypodermic syringe needles, such as those used by diabetics, to safely dispose of the used syringe by depositing used syringes through an opening specifically designed and shaped to receive hypodermic syringes so that no objects of greater breadth than the syringe barrel will fit into the collection chamber 19 of the container.

FIG. 1 also shows a self-supporting, conically-shaped insert 32 which abuts and conforms to the shape of the lower cylindrical side wall 15. This insert can be shaped and textured to be penetrated by the needle points 27 of the syringes 29 so that the syringes remain in substantially the same position as when the syringes were first deposited into the collection chamber. Additionally, the side wall of the container and the insert are shaped, textured, and designed so that once deposited into the collection chamber of the container, the syringes cannot turn end-for-end. For example, the collection chamber can be designed to be of a breadth which is less than the length of the syringes so that once the syringe are inserted into the collection chamber, the syringes cannot turn end-for-end.

Figure 2:
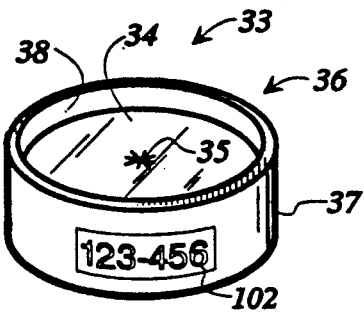
FIG. 2 is a perspective view of a transparent top wall means of another embodiment of the present invention.

FIG. 2 is another embodiment 33 of the present invention showing a single-wall transparent top wall means 34 defining a scored portion 35 for receiving used hypodermic syringes. This embodiment can take the same general configuration as the above-described embodiment, including a telescoping cover 36 which comprises a cylindrical side wall 37 with inwardly projecting seats 38 holding the transparent top wall 34 in position. This embodiment of the present invention including the transparent top wall is particularly desirable for accountability purposes, such as for a pharmacist or a diabetic patient, who can visually inspect the number of used syringes deposited into the collection chamber of the container so as to determine the fullness of the container.

FIG. 6 is another embodiment 40 of the present invention, showing the same general exterior construction as the embodiment 10 FIG. 1, including a cylindrical container 41, comprising an upper telescopic cover 42, which telescopes about a lower cylindrical side wall 44. The telescopic cover 42 discloses a single-wall top wall means 45 which defines an opening 46 therein, formed preferably by score lines 47. The score lines 47 are sized so that hypodermic needle syringes fit snugly through the opening with a tight and yielding fit so as to avoid inadvertent escape of the syringe and particularly to avoid inserting objects of greater internal breadth than a hypodermic syringe. Additionally, this embodiment provides an inwardly and downwardly conically shaped inner wall 48 with portions of the inner wall 48 abutting a bottom wall 50 of the container. The conically shaped inner wall can extend from the bottom wall 50 upwards to a height less than or equal to the height of the cylindrical side wall 44. A holding chamber 51 is defined by the cylindrical side wall 44 and the inner conically shaped wall 48. A cork 52 or other means for being partially penetrated by, and therefore retaining hypodermic needle syringes is positioned in the lower portion of the holding chamber 51, and can be positioned in a central location between the conically shaped inner wall 48.

FIGS. 7, 8, 9 and 10 show a rectangularly shaped embodiment 55 of the system for collecting and disposing of hypodermic needle syringes. This embodiment comprises four flaps A, B, C, and D, (FIG. 10) folded at vertical dashed lines and at right angles to each other to form four rectangular side walls (FIG. 8). An edge 54 can extend from one of the flaps so as to connect the four side wall together, such as by adhesive connection. Moreover, the four flaps include an upper portion 56 and a lower portion 57 which form a top wall 58 and a bottom wall 59 of the container when folded along the horizontal line. Flaps B and D have slightly shorter flaps 60 on the upper portions 56 of the flaps, and when folded inwardly and at right angles to the side walls of B and D form an inner top wall 63 (FIG. 7) having a space 62 of a size that corresponds to the largest cross-sectional breadth of a hypodermic syringe is formed between the two opposing short flaps 60. Flaps A and C have upper flaps 65 on the upper portion 56 which come together when folded inwardly and at right angles to the side walls A and C, and the flaps 65 have scores or cuts 66 within the flaps which form an outer wall 67 (FIG. 7), registering with the space 62 formed by the two shorter flaps 60. The flaps 65 with the cuts 66 being of a size that corresponds to the largest cross-sectional breadth of a hypodermic syringe becomes the outer wall 67 of the top wall 58 of the container, and whereby all four flaps form a top wall opening 68. Additionally, the top wall 58, bottom wall 59, and four side walls A, B, C and D define a collection chamber 69 for syringes 29 to be deposited into.

Figure 11:
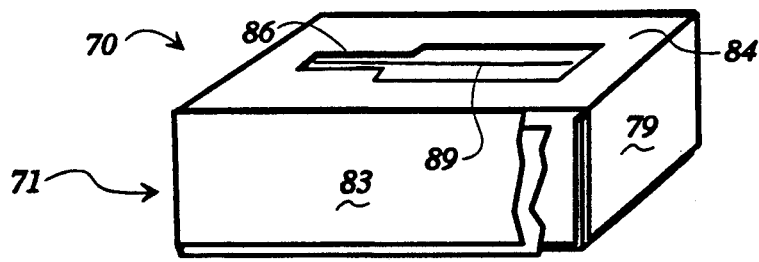
FIG. 11 is a perspective view of another embodiment of the present invention showing an opening specifically sized and shaped to receive a used syringe.
Figure 12:
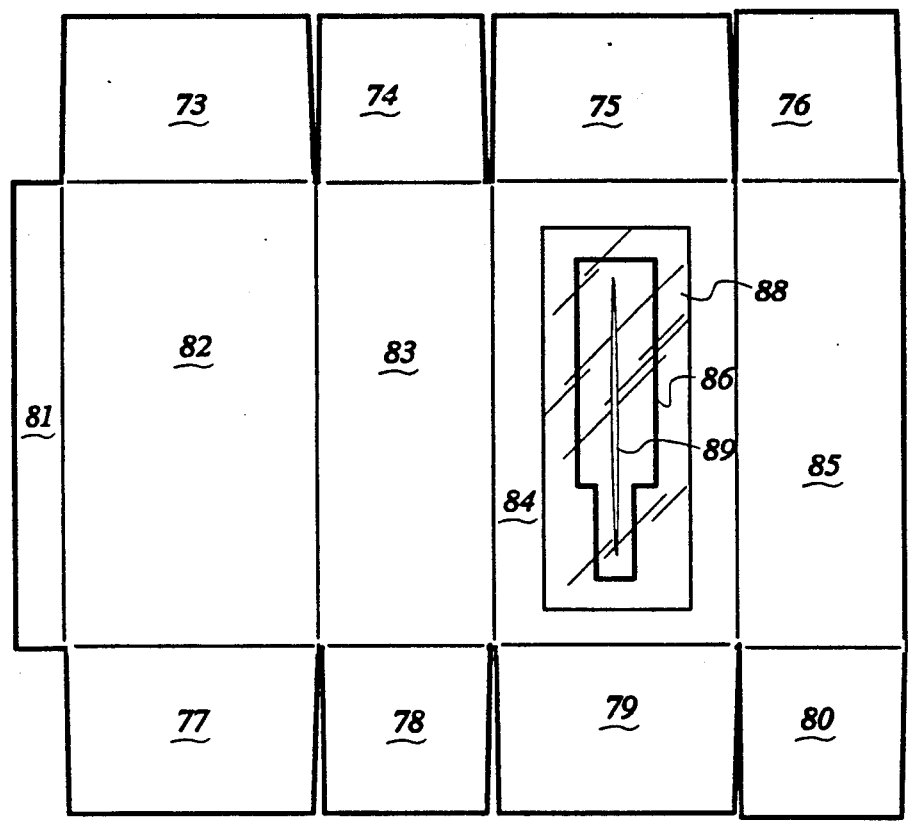
FIG. 12 is a plan view of the embodiment of FIG. 11 shown unassembled.

FIG. 11 shows another embodiment or container 70 including a housing 71 being formed if end wall flaps 73, 74, 75, 76, 77, 78, 79 and 80, a tab 81, a top wall 84, a bottom wall 82, and side walls 83 and 85, all of which are most clearly shown in FIG. 12, whereby the end wall flaps, tab, top wall, bottom wall and side walls are folded inwardly and at right angles ton one another at the fold lines to form a rectangularly-shaped container with a rectangularly-shaped collection chamber. This embodiment shows the top wall 84 being spaced and parallel to the bottom wall 82 and the side wall 83 being spaced and parallel to side wall 85. The tab 81 connects the bottom wall 82 to the side wall 85, by means such as adhesives. The end wall flaps 74, 76, 78 and 80 of the side walls 83 and 85 are folded inwardly at their fold lines to form an inner end wall for the housing 71. Outer end walls are formed by the end wall flaps 73, 75, 77, and 79 which are folded at their horizontal fold lines, whereby flap 75 overlaps flap 73 and flap 79 overlaps 77. This embodiment provides a tripe end wall construction to protect hypodermic syringe users and others in their environment from skins scratch or puncture of a used syringe, after depositing into the container.

The top wall 84 of this embodiment includes an opening 86 sized and shaped of approximately the same cross-sectional breadth and width of a used syringe. The opening 86 has a substantially transparent sheet material 88 covering the opening so that the user can see through the sheet material 88 and into a collection chamber of the container. A slit 89 is formed so that the used syringes can enter the opening 86 and can deposit the syringe into the collection chamber.

Figure 13:
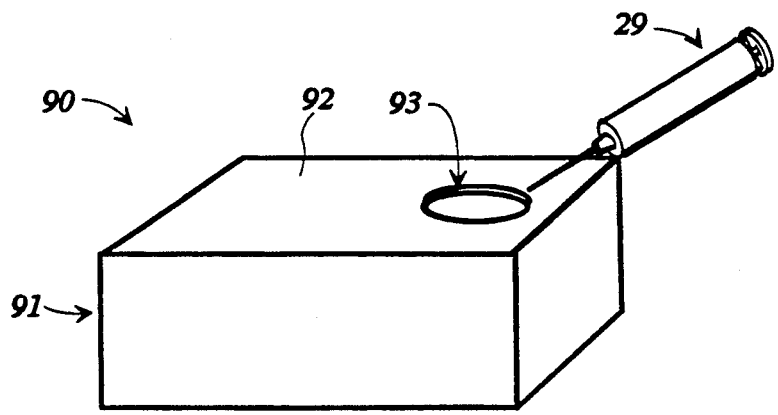
FIG. 13 is a perspective view of another embodiment of the invention showing an elongated opening for receiving used syringes.

FIG. 13 shows another embodiment 90 with a rectangularly-shaped container or housing 91 being conventionally formed, such as in the same manner as the embodiment 70, having flaps or end walls and side walls of generally the same configuration as the embodiment 70 of the container. A top wall 92 defines an elongated opening 93 for the syringe 29 to be deposited into a rectangular collection chamber of the container at an angle. this diagonal insertion of the used syringes causes the syringes to maintain its same general position as when inserted into the rectangular collection chamber and causes the needle points of the syringes to be positioned in substantially the same direction. This embodiment 70 also provides for a container that is sized, shaped, and designed so that once deposited into the collection chamber, the used syringes will not turn end-for end.

All of the above-described embodiments of the container system can include indicia means which identify the container as being a hazardous items disposal area. The indicia is located on the exterior side of the container and can designate the personal-use hypodermic syringe container by methods such as color-coding, labelling 101 (FIG. 3), serializing 102 (FIG. 2), and texturing 101 (FIG. 3) the container, or any combinations of these methods. Additionally, a counter mechanism can be inserted on the exterior side of the container to count each used syringe by means of a pressure detector, as each used syringe is being deposited into the collection chamber of the container.

The material of construction in all of the above-described embodiments of the invention can comprise non-biodegradable thermoplastic resins selected from the following preferred group: polypropylene, polyethylene, polystyrene, acrylonitrile-butadiene, styrene (ABS), and polycarbonate. These thermoplastic resins are substantially leak-resistant and puncture resistant and can form any of the above described embodiments by means of injection molding.

The material of construction in all or a portion of the above-described embodiments can also comprise biodegradable, or otherwise known as non petroleum-based materials selected from the following group: natural cellulosic-based materials such as wood, cardboard, particle board and fiber board, non-natural cellulosic materials, such as rayon, cellophane, and cellulose-nitrate, and other materials, such as natural rubber and natural wax which when burned emit no more than trace amounts of sulfur or chlorine. These materials will form a clean-burning container, which may aid in the compliance of future incineration regulations for hypodermic syringes.

Additionally, the material of construction for the container can be tailored so that a combination of biodegradable and non-biodegradable materials can be used. Thus, the biodegradable or burnable material when combined with the non-biodegradable material can be of sufficient mass and constructed of such a geometry in comparison to the volume an shape of the collection chamber so that when ignited and burned, can be sufficient to render any plastic materials within the collection chamber of the container.

While the invention has been described in relation to these preferred embodiments, it will be apparent to those skilled in the art that the invention is susceptible to additional embodiments without departing from the spirit and scope of the invention. Therefore, it is intended that the invention not be limited except by the claims.

We claim:

1. A container for collecting and disposing of hypodermic syringes of the type used to inject insulin into diabetic persons, said needle syringes being of an approximate predetermined length, breadth and cross-sectional shape, and said container comprising:
   a bottom wall,
   a side wall extending at an angle from said bottom wall,
   a top wall closing the other end of said side wall,
   said bottom wall, side wall, and top wall defining a collection chamber,
   an opening defined through said container with the opening corresponding in breadth and shape to the breadth and shape of the insulin syringes so as to receive the insulin syringes when inserted longitudinally through said opening and prohibiting the receipt of other objects of greater breadth,
   said top wall being spaced from said bottom wall a distance that forms the collection chamber with a length greater than the length of the needle syringes when the plungers of the syringes are inserted to their innermost positions of the cylinders of the syringes so that the syringes can be fully received between said top wall and said bottom wall in the collection chamber, said container being cylindrical and comprising a cylindrical side wall having a first and a second end, said first and second ends turned in to form inwardly projecting seats, and said top wall and said bottom wall at said first and second ends of said container supported by said seats; and said container including means for maintaining the syringes oriented in substantially the same orientation within the collection chamber so that the syringes cannot turn end-for-end in the container.

2. The container of claim 1 and wherein at least some of said bottom wall, side wall, and top wall are fabricated of a cellulosic material of sufficient mass and constructed of such a geometry in comparison to the volume and shape of the collection chamber so that if ignited and burned is sufficient to render any plastic materials of the syringes in the collection chamber.

3. The container of claim 1 and wherein said container is fabricated of burnable means of sufficient mass and constructed of such a geometry in comparison to the volume and shape of the collection chamber so that when ignited and burned, the burnable means will render any plastic materials of all syringes in the collection chamber.

4. A container for collecting and disposing of hypodermic needle syringes of the type used to inject insulin into diabetic persons, and said needle syringes are of an approximate predetermined length, breadth and cross-sectional shape, and said container comprising:
a bottom wall,
a side wall extending at an angle from said bottom wall,
a top wall closing the other end of said side wall,
said bottom wall, side wall, and top wall defining a collection chamber,
an opening defined through said container with the opening corresponding in breadth and shape to the breadth and shape of the needle syringes so as to receive the syringes when inserted longitudinally through said opening and prohibiting the receipt of other objects of greater breadth,
said top wall being spaced from said bottom wall a distance that forms the collection chamber with a length greater than the length of the needle syringes when the plungers of the syringes are inserted to their innermost positions of the cylinders of the syringes so that the syringes can be fully received between said top wall and said bottom wall in the collection chamber,
said top wall comprises a pair of overlying disks, with a first one of said disks defining said opening of a breadth and shape that corresponds to the breadth and shape of the largest cross-section of the syringes, and a second pair of said disks defining a second opening aligned with the opening of said first disk formed by a circular array of flaps that normally substantially close said second opening and which flex inwardly of the collection chamber in response to a syringe being pushed needle first through the aligned opening into the collection chamber and which retard the movement of a syringe falling through the aligned openings out of the collection chamber, and
said container including means for maintaining the syringes oriented in substantially the same orientation within the collection chamber so that the syringes cannot turn end-for-end in the container.

5. The container of claim 1 and wherein said top wall is formed with slits that define an array of flaps that when bent from the top wall opening, form a check valve opening.

6. The container of claim 1 and further including an insert contained in said collection chamber of said container for the used needle-end of the syringes to pierce when deposited into the collection chamber.

7. The container of claim 6 and wherein the material of said insert conforms to the shape of the container.

8. The container of claim 6 and wherein said insert is formed in a self-supporting shape that fits a lower portion of the collection chamber of the container.

9. The container of claim 6 and wherein said insert is formed essentially of a combustible material so as to enhance combustion of the container when burned.

10. The container of claim 6 and wherein said insert is shaped and textured to be penetrated by sharp points of syringes, such as by needle points of insulin needle syringes.

11. A container for collecting and disposing of hypodermic needle syringes of the type used to inject insulin into diabetic persons, and said needle syringes are of an approximate predetermined length, breadth and cross-sectional shape, and said container comprising:
a bottom wall,
a side wall extending at an angle from said bottom wall,
a top wall closing the other end of said side wall,
said bottom wall, side wall, and top wall defining a collection chamber,
an opening defined through said container with the opening corresponding in breadth and shape to the breadth and shape of the needle syringes so as to receive the syringes when inserted longitudinally through said opening and prohibiting the receipt of other objects of greater breadth,
an insert contained in said collection chamber of said container for the used needle-end of the syringes to engage when deposited into the collection chamber, said insert is fabricated with a conically-shaped receptacle to cause the deposited syringes to slope outwardly from the center of said container, when the syringes are deposited into the collection chamber,
said top wall being spaced from said bottom wall a distance that forms the collection chamber with a length greater than the length of the needle syringes when the plungers of the syringes are inserted to their innermost positions of the cylinders of the syringes so that the syringes can be fully received between said top wall and said bottom wall in the collection chamber, and
said container including means for maintaining the syringes oriented in generally the same orientation within the collection chamber so that the syringes cannot turn end-for-end in the container.

12. The container of claim 4 and wherein at least some of said bottom wall, side wall, and top wall are fabricated of a cellulosic material of sufficient mass and constructed of such a geometry in comparison to the volume and shape of the collection chamber so that if ignited and burned is sufficient to render any plastic materials of the syringes in the collection chamber.

13. The container of claim 4 and wherein said container is fabricated of burnable means of sufficient mass and constructed of such a geometry in comparison to the volume and shape of the collection chamber so that if ignited and burned, the burnable means will render any plastic materials of all syringes in the collection chamber.

14. The container of claim 4 and wherein said top wall is formed with slits that define an array of flaps that when bent from the top wall opening, form a check valve opening.

15. The container of claim 4 and further including an insert contained in said collection chamber of said container for the used needle-end of the syringes to pierce when deposited into the collection chamber.

16. The container of claim 15 and wherein the material of said insert conforms to the shape of the container.

17. The container of claim 15 and wherein said insert is formed in a self-supporting shape that fits a lower portion of the collection chamber of the container.

18. The container of claim 15 and wherein said insert is formed essentially of a combustible material so as to enhance combustion of the container when burned.

19. The container of claim 15 and wherein said insert is shaped and textured to be penetrated by sharp points of syringes, such as by needle points of insulin needle syringes.

20. The container of claim 11 and wherein at least some of said bottom wall, side wall, and top wall are fabricated of a cellulosic material of sufficient mass and constructed of such a geometry in comparison to the volume and shape of the collection chamber so that if ignited and burned is sufficient to render any plastic materials of the syringes in the collection chamber.

21. The container of claim 11 and wherein said container is fabricated of burnable means of sufficient mass and constructed of such a geometry in comparison to the volume and shape of the collection chamber so that if ignited and burned, the burnable means will render any plastic materials of all syringes in the collection chamber.

22. The container of claim 11 and wherein said top wall is formed with slits that define an array of flaps that when bent from the top wall opening, form a check valve opening.

23. The container of claim 11 and further including an insert contained in said collection chamber of said container for the used needle-end of the syringes to pierce when deposited into the collection chamber.

24. The container of claim 23 and wherein the material of said insert conforms to the shape of the container.

25. The container of claim 23 and wherein said insert is formed in a self-supporting shape that fits a lower portion of the collection chamber of the container.

26. The container of claim 23 and wherein said insert is formed essentially of a combustible material so as to enhance combustion of the container when burned.

27. The container of claim 23 and wherein said insert is shaped and textured to be penetrated by sharp points of syringes, such as by needle points of insulin needle syringes.

* * * * *